United States Patent [19]

Krstenansky et al.

[11] Patent Number: 6,005,071
[45] Date of Patent: Dec. 21, 1999

[54] ANTICOAGULANT PEPTIDES

[75] Inventors: John L. Krstenansky, Cincinnati; Simon J. T. Mao, Loveland, both of Ohio

[73] Assignee: Merrell Pharmaceuticals Inc., Bridgewater, N.J.

[21] Appl. No.: 09/022,738

[22] Filed: Feb. 12, 1998

Related U.S. Application Data

[62] Division of application No. 08/412,356, Mar. 28, 1995, Pat. No. 5,789,540, which is a continuation of application No. 08/126,441, Sep. 23, 1993, abandoned, which is a continuation of application No. 07/989,998, Dec. 10, 1992, abandoned, which is a continuation of application No. 07/774,126, Oct. 11, 1991, abandoned, which is a continuation of application No. 07/559,438, Jul. 26, 1990, abandoned, which is a continuation of application No. 07/388,725, Aug. 1, 1989, abandoned, which is a continuation of application No. 07/138,611, Jan. 12, 1988, abandoned, which is a continuation-in-part of application No. 07/053,162, May 21, 1987, abandoned, which is a continuation-in-part of application No. 07/006,417, Jan. 23, 1987, abandoned.

[51] Int. Cl.⁶ ..................................................... C07K 7/00
[52] U.S. Cl. ..................... 530/326; 530/324; 530/325; 530/327; 530/328
[58] Field of Search ..................................... 530/324, 325, 530/326, 327, 328

[56] References Cited

U.S. PATENT DOCUMENTS

| | | | |
|---|---|---|---|
| 3,720,690 | 3/1973 | Fritz et al. | 260/345.2 |
| 4,499,082 | 2/1985 | Shenvi et al. | 514/2 |
| 4,638,047 | 1/1987 | Szelke et al. | 530/332 |
| 4,654,302 | 3/1987 | Fritz et al. | 435/70 |
| 4,668,662 | 5/1987 | Tripier et al. | 514/12 |
| 4,737,487 | 4/1988 | Watts et al. | 514/15 |
| 4,745,177 | 5/1988 | Fritz et al. | 530/324 |
| 5,192,747 | 3/1993 | Krstenansky | 514/15 |
| 5,541,161 | 7/1996 | Krstenansky et al. | 514/14 |

FOREIGN PATENT DOCUMENTS

| | | |
|---|---|---|
| 0158986 | 10/1985 | European Pat. Off. . |
| 0225633 | 6/1987 | European Pat. Off. . |
| 0276014 | 7/1988 | European Pat. Off. . |
| 3445532 | 6/1983 | Germany . |
| 3445517 | 6/1986 | Germany . |

OTHER PUBLICATIONS

Krstenansky, et al., *Chemical Abstract*, vol. 107 No. 97113C (1987).
Derwent Ab. 86–162807/26. W. German Patent Appln No. 3445532, published Jun. 19, 1986.
Derwent Ab. 86–162802/26. W. German Patent Appln. No. 3445517, published Jun. 19, 1986.
Krstenansky, et al., *FEBS letter* 211(1) 10–16 (1987).
Mao, et al., *Anal. Biochem.* 161, 514–18 (1987).
Owen, *J. Med. Chem.*, 31, 1009–1011 (1988).
Baskova, et al., *Thromb.Res.* 30(5):459–467 (1983).
Markwardt, *Biomed.Biochim. Acta.* 44(7–8):1007–1013 (1985).
Akbar, et al., *Haemostasis* 6(1):59–71 (1977).
Hoffmann, et al.,*Haemostasis* 14(2):164–169 (1984).
Minar, et al., *Klin Wochenschr* 63(4):190–191 (1985).
Sutor, et al., KontrolleAntithrombotika, Hamb.Symp. Blutgerinnung, 23rMtg 1980, 117–123.
Hastbacka, et al., *Nord.Med* 77(14):445–450 (1967).
Budzynski, et al., *Proc. Soc.Exp. Biol. Med* 168(2):266–275 (1981).
Markwardt, et al., *Thromb.Haemost.* 52(2): 160–163 (1984).
Markwardt, et al., *Thromb.Haemost.* 47(3):226–229(1982).
Markwardt, et al., *Thromb.Haemost.* 49(3):235–237(1983).
Wu, et al., *Thromb.Haemost.* 35(3):702–711(1976).
Brown, et al., *Thromb. Res.* 17(1–2):267–272 (1980).
Markwardt, et al., *Thromb.Res.* 11(3):275–283(1977).
Ishikawa, et al., *Thromb.Res.* 19(3):351–358(1980).
Neal, et al., *Thromb.Res.* 16(3–4):473–484(1979).
Krstenansky, et al.,*Peptides: Chemistry and Biology*; Tenth American Peptide Symposium,St. Louis, Mo, May. 23–28(1987), Escom SciencePublishers B.V.: Leiden, Netherlands.
Krstenansky, et al., *Thrombosis Research* 52:137–141 (1988).
Krstenansky, et al., *Thrombosis Research* 54:319–325 (1989).
Krstenansky, et al., *Thrombosis and Haemostasis* (Stuttgart) 63(2):208–214 (1990).
Krstenansky, et al., *Chemical Abstracts* 109:231560t, p.918 (1988).
Dayhoff, et al., *Atlas of Protein Sequence and Structure*, "A Model of Evolutionary Change in Protein", vol. 5:90–99 (1972).
HCAPLUS DN 96:16236, Reid et al., Dev. Biochem. 14(Calcium–Binding Proteins), 337–341, 1980.

*Primary Examiner*—Michael P. Woodward
*Assistant Examiner*—C. Delacroix-Muirheid
*Attorney, Agent, or Firm*—T. Helen Payne

[57] ABSTRACT

This invention relates to peptide derivatives which are useful anticoagulant agents.

34 Claims, No Drawings

ANTICOAGULANT PEPTIDES

This application is a divisional of application Ser. No. 08/412,356, filed Mar. 28, 1995, now U.S. Pat. 5,789,540, which is a continuation of application Ser. No. 08/126,441, filed Sep. 23, 1993, now abandoned, which is a continuation of application Ser. No. 07/989,998, filed Dec. 10, 1992, now abandoned, which is a continuation of application Ser. No. 07/774,126, filed Oct. 11, 1991, now abandoned, which is a continuation of application Ser. No. 07/559,438, filed Jul. 26, 1990, now abandoned, which is a continuation of application Ser. No. 07/388,725, filed Aug. 1, 1989, now abandoned, which is a continuation of application Ser. No. 07/138,611, filed Jan. 12, 1988, now abandoned, which is a continuation-in-part of application Ser. No. 07/053,162, filed May 21, 1987, now abandoned, which is a continuation-in-part of application Ser. No. 07/006,417, filed Jan. 23, 1987, now abandoned, which are herein incorporated by reference.

FIELD OF INVENTION

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense and allergic reactions which commonly follow administration of any foreign protein of this size.

Applicants have discovered a specific region of hirudin that is responsible, at least in part, for its anticoagulant activity. This region has been chemically synthesized and certain of its analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation. The peptides of this invention possess significant anticoagulant activity and their unusual ability to bind only to the recognition site without binding to the cleavage site of thrombin may allow for a scientifically interesting and therapeutically significant adjunct to anticoagulant therapy.

SUMMARY OF THE INVENTION

Peptide derivatives of the formula

wherein

X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;

$A_1$ is a bond or is a peptide containing from 1 to 11 residues of any amino acid;

$A_2$ is Phe, SubPhe, -(2- and 3-thienyl)alanine, -(2-and 3-furanyl)alanine, -(2-, 3-, and 4-pyridyl)alanine, -(benzothienyl-2- and 3-yl)alanine, -(1- and 2-naphthyl)alanine, Tyr or Trp;

$A_3$ is Glu or Asp;

$A_4$ is any amino acid;

$A_5$ is Ile, Val, Leu, Nle, or Phe;

$A_6$ is Pro, Hyp, 3,4-dehydroPro, thiazolidine-4-carboxylate, Sar, NMePgl or D-Ala;

$A_7$ is any amino acid;

$A_8$ is any amino acid;

$A_9$ is a lipophilic amino acid selected from Tyr, Trp, Phe, Leu, Nle, Ile, Val, Cha and Pro or is a dipeptide containing at least one of these lipophilic amino acids;

$A_{10}$ is a bond or is a peptide fragment containing from one to five residues of any amino acid; and Y is a carboxy terminal residue selected from OH, $C_1$–$C_6$ alkoxy, amino, mono- or di-($C_1$–$C_4$) alkyl substituted amino, or benzylamino; are useful anticoagulant agents.

DETAILED DESCRIPTION OF THE INVENTION

The following common abbreviations of the amino acids are used throughout this specification:

Gly-glycine
Ala-alanine
Val-valine
Leu-leucine
Ile-isoleucine
Cha-cyclohexylalanine
Orn-ornithine
Pro-proline
Phe-phenylalanine
Trp-tryptophan
Met-methionine
Ser-serine
Thr-threonine
Cys-cysteine
Tyr-tyrosine
Asn-asparagine
Gln-glutamine
Asp-aspartic acid
Glu-glutaminc acid
Lys-lysine
Arg-arginine
His-histidine
Nle-norleucine
Hyp-hydroxyproline
Glt-glutaryl
Mal-maleyl
Npa--(2-naphthyl)alanine
3,4-dehydroPro-3,4-dehydroproline
Tyr($SO_3H$)-tyrosine sulfate
Pgl-phenylglycine NMePgl-N-methyl-phenylglycine Sar-sarcocine (N-methylglycine)

pSubPhe-para substituted phenylalanine

SubPhe-ortho, meta, or para, mono- or di- substituted phenylalanine

DAla-D-alanine

Ac-acetyl

Suc-succinyl pClPhe-para-chloro-phenylalanine pNO$_2$Phe-para-nitro-phenylalanine An alkyl group and the alkyl portion of an alkoxy group is taken to include straight, branched, or cyclic alkyl groups, for example, methyl, ethyl, propyl, isopro- pyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl A halogen group is a fluoro, chloro, bromo or iodo group.

The term "any amino acid" as used herein includes the naturally occurring amino acids as well as other "non-protein" -amino acids commonly utilized by those in the peptide chemistry arts when preparing synthetic analogs of naturally occurring peptides. The naturally occurring amino acids are glycine, alanine, valine, leucine,isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" -amino acids are norleucine, norvaline, alloisoleucine, homoarginine, thiaproline, dehydroproline, hydroxyproline (Hyp), homoserine, cyclohexylglycine (Chg), -amino-n-butyric acid (Aba), cyclohexylalanine (Cha), aminophenylbutyric acid (Pba), phenylalanines substituted at the ortho, meta, or paraposition of the phenyl moiety with one or two of the following, a (C$_1$–C$_4$) alkyl, (C$_1$–C$_4$) alkoxy, halogen, or nitro groups or substituted with a methylenedioxy group, 2- and 3-thienylalanine, -2- and 3-furanylalanine, -2-, 3-, and 4-pyridylalanine, -(benzothienyl-2- and 3-yl)alanine, -(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids.

The term "lipophilic amino acid" includes Tyr, Phe, Leu, Nle, Ile, Val, His and Pro.

The natural amino acids with the exception of glycine, contain a chiral carbon atom. Unless otherwise specifically indicated, the optically active amino acids, referred to herein, are of the L-configuration,. For example, any of the amino acids of the $A_1$ or $A_{10}$ group can be of the D- or L-configuration. As is customary, the structure of peptides written out herein is such that the amino terminal end is on the left side of the chain and the carboxy terminal end is on the right side of the chain.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

As with any generic group of chemical compounds, certain groups are preferred. Applicants prefer those peptide derivatives of formula 1 wherein X is hydrogen, acetyl, or succinyl.

Also preferred are those formula 1 compounds wherein $A_1$ is Thr-Pro-Lys-Pro-Gln-Ser-His-Asn-Asp-Gly-Asp, -Ser-Thr-Pro-Asn-Pro-Glu-Ser-His-Asn-Asn-Gly-Asp-, -His-Asn-Asp-Gly-Asp-, -Asn-Asp-Gly-Asp-, -Asp-Gly-Asp-, -Gly-Asp-. -Asp-, or a bond.

$A_2$ is preferably Phe, -2- or 3-thienylalanine, Tyr, Trp, Npa or pClPhe;

$A_3$, Glu;

$A_4$, Glu, Asp, Pro or Ala;

$A_5$, Ile, Leu;

$A_6$, Pro, Sar, D-Ala, Hyp or NMePgl;

$A_7$, Glu, Gln, Asp or Ala;

$A_8$, Glu, Asp or Ala;

$A_9$, Pro, Ala-Tyr, Ala-Cha, Tyr-Cha, Tyr-Leu, Ala-Phe, Tyr-Tyr;

$A_{10}$, Glu, Asn, Asp-Glu, Pro, Gln, Ala, a bond, D-Lys, Lys, D-Asp or Orn; and Y, OH or NH$_2$.

Especially preferred are those peptide derivatives of formula 1 wherein either X is acetyl and $A_1$ is Gly-Asp or Asp or X is succinyl and $A_1$ is a bond and wherein $A_2$, is Phe; -(2-thienylalanine) or Tyr;

$A_3$, Glu;

$A_4$, Glu or Pro;

$A_5$, Ile;

$A_6$, Pro;

$A_7$, Glu;

$A_8$, Glu or Asp;

$A_9$, Tyr-Leu, Ala-Tyr, Tyr-Tyr, Ala-Phe,Ala-Cha or Pro;

$A_{10}$, Gln; Asp; Pro; a bond; D-Asp, D-Lys, D-Glu or -Asp-Glu; and

Y, OH or NH$_2$.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an -amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced -amino protected amino acid.

An example of a hydroxymethyl resin is described by Bodanszky, et al., *Chem. Ind. (London)* 38, 1597–98 (1966).

A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta,* 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the -amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific -amino protecting groups may be used. After removal of the -amino protecting group the other amino protected amino acids are coupled step-wise in the desired order. Alternatively, multiple amino acid groups may be coupled by the solution method prior to coupling with the resin supported amino acid sequence.

The -amino protecting group employed with each amino acid introduced into the polypeptide sequence may be any such protecting group known to the art. Among the classes of -amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and -chlorobutyryl; (2) aromatic urethan type protecting groups such as benzyloxycarbonyl and substituted benzyloxycarbonyl, such as p-chlorobenzyloxycarbonyl, p-nitrobenzyl-carbonyl, p-bromobenzyloxycarbonyl, p-methoxybenzyloxycarbonyl, 1-(p-biphenylyl)-1-methylethoxy-carbonyl, -dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred -amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.,* 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a fourfold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the -amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the -amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

The anticoagulant dose of a peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

Example 1

Preparation of H-Gly-Asp-Phe-Glu-Glu-Ile-Pro-Glu-Glu-Tyr-Leu-Gln-OH

The peptide was snythesized by solid-phase methods using 0.1 mmol of a 0.66 mmol/g Boc-Gln-PAM resin. Double symmetrical anhydride couplings were performed with 2.0 mmol N-Boc-amino acid (Peptides International) except in the case of Boc-Gln, which was coupled by the DCC/HOBT method. The side chain protection utilized was: Asp(Chx), Glu(Bzl), Tyr(2-BrZ). Upon completion of the synthesis the N-Boc protection was removed with 50% trifluoroacetic acid in methylene chloride. The resin was washed three times with methylene chloride, neutralized with three washings of 10% diisopropylethylamine in methylene chloride, washed three times with methylene chloride, and dried in vacuo. The peptide was deprotected and cleaved from the resin with HF containing 2% anisole at 0° C., for 35 min. The HF was removed in vacuo at 0° C., the peptide precipitated with ethyl ether, extracted from the resin with 30% aqueous acetic acid and lyophilized.

The peptide was purified by desalting on a 92×2.6 cm Sephadex G-15 column in 5% aqueous acetic acid and lyophilized. Preparative HPLC was performed on a $C^{18}$ Vydac 218TP1010 (250×10 mm) column with 24% acetonitrile in 0.1% aqueous trifluoroactic acid at 5 ml/min. The major peak was collected and lyophilized leaving 101 mg of the desired produce (58% yield based on initial resin substitution). Homogeneity was determined by HPLC and TLC. HPLC Vydac 218TP54 (250×4.6 mm) $C^{18}$ column, 2 ml/min, $t_o$=1.9 min: time of elution with a 15–40% acetonitrile in 0.1% trifluoroacetic acid linear gradient at 1%/min. (HPLC) is 14.4 min.

TLC: [Merck 5715 20×20 cm Silica gel 60 plates (0.25 mm thickness)] n-butanol/actic acid/water/pyridiene (6:1.2:4.8:6) (TLC I) Rf=0.42; isopropanol/conc. ammonium hydroxide/water (3:1:1) (TLC II) Rf=0.32; n-butanol/acetic acid/water (4:5:5) (TLC III) Rf=0.70. FAB-MS: (M+H)–1468.4±1 m$\mu$ (calcd. 1468.6). Amino acid analysis: (6N HCl hydrolysis; 24 hr. at 106° C.). Asx 1.03 (1); Glx 5.05 (5); Pro 1.03 (1); Gly 1.00 (1); Ile 0.97 (1); Leu 1.01 (1); Tyr 0.93 (1); Phe 0.98 (1); NH3 1.06 (1). 280=1254. 85% peptide content by weight.

In the same manner, the peptides of the following example 2-32 were prepared.

Example 2

Ac-Ser-His-Asn-Asp-Gly-Asp-Phe-Glu-Glu-Ile-Pro-Glu-Glu-Tyr-Leu-Gln-OH

Example 3

H-Asn-Asp-Gly-Asp-Phe-Glu-Glu-Ile-Pro-Glu-Glu-Tyr-Leu-Gln-OH

Example 4

H-Asp-Phe-Glu-Glu-Ile-Pro-Glu-Glu-Tyr-Leu-Gln-OH

Example 5

H-Phe-Glu-Glu-Ile-Pro-Glu-Glu-Tyr-Leu-Gln-OH

Example 6

H-Asp-Phe-Glu-Ala-Ile-Pro-Glu-Glu-Tyr-Leu-Gln-OH

Example 7

H-Asp-Phe-Glu-Glu-Ile-Pro-Ala-Glu-Tyr-Leu-Gln-OH

Example 8

H-Asp-Phe-Glu-Glu-Ile-Pro-Glu-Glu-Tyr-Leu-Ala-OH

Example 9

H-Asp-Phe-Glu-Glu-Ile-Pro-Glu-Glu-Leu-Ala-OH

Example 10

Ac-Asp-Phe-Glu-Glu-Ile-Pro-Glu-Glu-Tyr-Leu-Gln-OH

Example 11

Ac-Gly-Asp-Phe-Glu-Glu-Ile-Pro-Glu-Glu-Tyr-Leu-Gln-OH

Example 12

Suc-Phe-Glu-Glu-Ile-Pro-Glu-Glu-Tyr-Leu-Gln-OH

Example 13

H-Asp-Phe-Glu-Glu-Ile-Pro-Glu-Glu-Tyr-Leu-NH$_2$

Example 14

H-Gly-Asp-Tyr-Glu-Glu-Ile-Pro-Glu-Glu-Tyr-Leu-Gln-OH

Example 15

H-Gly-Asp-Trp-Glu-Glu-Ile-Pro-Glu-GLu-Tyr-Leu-Gln-OH

Example 16

H-Gly-Asp-pClPhe-Glu-Glu-Ile-Pro-Glu-Glu-Tyr-Leu-Gln-OH

Example 17

H-Gly-Asp-pNO$_2$Phe-Glu-Glu-Ile-Pro-Glu-Glu-Tyr-Leu-Gln-OH

Example 18

H-Gly-Asp-Phe-Glu-Glu-Ile-Sar-Glu-Glu-Tyr-Leu-Gln-OH

Example 19

H-Gly-Asp-Phe-Glu-Glu-Ile-DAla-Glu-Glu-Tyr-Leu-Gln-OH

Example 20

H-Gly-Asp-Phe-Glu-Glu-Ile-Hyp-Glu-Glu-Tyr-Leu-Gln-OH

Example 21

H-Gly-Asp-Phe-Glu-Glu-Ile-NMePgl-Glu-Glu-Tyr-Leu-Gln-OH

Example 22

H-Gly-Asp-Phe-Glu-Pro-Ile-Pro-Glu-Asp-Ala-Tyr-Asp-Glu-OH

Example 23

H-Ser-His-Asn-Asp-Gly-Asp-Phe-Glu-Glu-Ile-Pro-Glu-Glu-Tyr-Leu-Gln-OH

Example 24

H-Gly-Asp-Phe-Glu-Pro-Ile-Pro-Glu-Asp-Ala-Tyr-Pro-NH$_2$

Example 25

Suc-Phe-Glu-Pro-Ile-Pro-Glu-Asp-Ala-Tyr-Pro-NH$_2$

Example 26

H-Asp-Phe-Glu-Pro-Ile-Pro-Glu-Glu-Ala-Tyr-Gln-OH

Example 27

H-Asp-Phe-Glu-Glu-Ile-Pro-Glu-Glu-Ala-Tyr-Glu-OH

Example 28

H-Asp-Phe-Glu-Glu-Ile-Pro-Glu-Asp-Ala-Tyr-Gln-OH

Example 29

Suc-Phe-Glu-Pro-Ile-Pro-Glu-Glu-Tyr-Leu-Pro-NH$_2$

Example 30

H-Gly-Asp- -(2-thienyl)alanyl-Glu-Glu-Ile-Pro-Glu-Glu-Tyr-Leu-Gln-OH

Example 31

H-Gly-Ala-O-methyltyrosyl-Glu-Glu-Ile-Pro-Glu-Glu-Tyr-Leu-Gln-OH

Example 32

Suc-Phe-Glu-Pro-Ile-Pro-Glu-Glu-Pro-OH

Example 33

H-Asp-Phe-Glu-Glu-Ile-Pro-Glu-Ala-Tyr-Leu-Gln-OH

Example 34

H-Asp-Phe-Glu-Glu-Ile-Pro-Glu-Glu-Ala-Leu-Gln-OH

Example 35

H-Gly-Asp-Phe-Glu-Glu-Leu-Pro-Glu-Glu-Tyr-Leu-Gln-OH

Example 36

H-Gly-Asp-Phe-Glu-Glu-Val-Pro-Glu-Glu-Tyr-Leu-Gln-OH

Example 37

H-Gly-Asp-Phe-Glu-Glu-Phe-Pro-Glu-Glu-Tyr-Leu-Gln-OH

Example 38

H-Asp-Phe-Glu-Pro-Ile-Pro-Glu-Glu-Tyr-Leu-Gln-OH

Example 39

Suc-Phe-Glu-Pro-Ile-Pro-Glu-Glu-Tyr-Leu-Gln-OH

Example 40

H-Gly-Asp-Phe-Glu-Pro-Ile-Pro-Glu-Asp-Ala-Tyr-Glu-OH

Example 41

H-Gly-Asp-Phe-Glu-Glu-Ile-Pro-Glu-Asp-Ala-Phe-Asp-Glu-OH

Example 42

Ac-Phe-Glu-Glu-Ile-Pro-Glu-Glu-Tyr-Leu-Orn-NH$_2$

Example 43

H-Gly-Asp-Phe-Glu-Pro-Ile-Pro-Glu-Glu-Tyr-Tyr-Glu-OH

Example 44

H-Asp-Phe-Glu-Pro-Ile-Pro-Glu-Glu-Tyr-Tyr-Gln-OH

Example 45

Suc-Tyr-Glu-Pro-Ile-Pro-Glu-Glu-Ala-Phe-Lys-NH$_2$

Example 46

Suc-Tyr-Glu-Pro-Ile-Pro-Glu-Glu-Ala-Phe-D-Lys-NH$_2$

Example 47

Suc-Tyr-Glu-Pro-Ile-Pro-Glu-Glu-Ala-Phe-Orn-NH$_2$

Example 48

Suc-Tyr-Glu-Pro-Ile-Pro-Glu-Glu-Ala-Tyr-Lys-NH$_2$

Example 49

Suc-Tyr-Glu-Pro-Ile-Pro-Glu-Glu-Ala-Phe-Lys-OH

Example 50

Suc-Tyr-Glu-Pro-Ile-Pro-Glu-Glu-Ala-His-Lys-OH

Example 51

Suc-Tyr-Glu-Pro-Ile-Pro-Glu-Glu-Ala-Cha-Lys-NH$_2$

Example 52

Suc-Tyr-Glu-Pro-Ile-Pro-Glu-Glu-Leu-Phe-Lys-NH$_2$

Example 53

Suc-Tyr-Glu-Pro-Ile-Pro-Gln-Glu-Ala-Phe-Lys-NH$_2$

Example 54

Suc-Tyr-Glu-Pro-Ile-Pro-Glu-Glu-Ala-Phe-Glu-OH

Example 55

Suc-Tyr-Glu-Pro-Ile-Pro-Glu-Glu-Ala-Phe-Gln-OH

Example 56

Suc-Tyr-Glu-Pro-Ile-Pro-Glu-Glu-Ala-Cha-Asp-OH

Example 57

H-Gly-Asp-Phe-Glu-Pro-Ile-Pro-Glu-Asp-Ala-Tyr-D-Asp-OH

Example 58

Ac-Thr-Pro-Lys-Pro-Gln-Ser-His-Asn-Asp-Gly-Asp-Phe-Glu-Glu-Ile-Pro-Glu-Glu-Tyr-Leu-Gln-OH

Example 59

Ac-Thr-Pro-Asn-Pro-Glu-Ser-His-Asn-Asn-Gly-Asp-Phe-Glu-Glu-Ile-Pro-Glu-Glu-Tyr-Leu-Gln-OH

Example 60

Suc-Tyr-Glu-Pro-Ile-Pro-Glu-Ala-Cha-Asn-OH

Example 61

Suc-Tyr-Glu-Pro-Ile-Pro-Glu-Glu-Tyr-Cha-Gln-OH

Example 62

Suc-Tyr-Glu-Pro-Ile-Pro-Glu-Glu-Pro-Cha-D-Glu-OH

Example 63

Suc-Tha-Glu-Pro-Ile-Pro-Glu-Glu-Pro-Cha-D-Glu-OH

Example 64

Suc-Npa-Glu-Pro-Ile-Pro-Glu-Glu-Ala-Cha-D-Glu-OH

Example 65

Suc-Tyr-Glu-Pro-Ile-Pro-Glu-Glu-Ala-Cha-D-Glu-OH

Example 66

Mal-Tyr-Glu-Pro-Ile-Pro-Glu-Glu-Ala-Cha-D-Glu-OH

Example 67

Glt-Tyr-Glu-Pro-Ile-Pro-Glu-Glu-Ala-Cha-D-Glu-OH

Example 68

Fum-Tyr-Glu-Pro-Ile-Pro-Glu-Glu-Ala-Cha-D-Glu-OH

The peptides of examples 2–63 have the following properties:

| EXAMPLE NO. | His | Asx | Ser | Glx | Pro | Ala | Gly | Ile | Leu | Tyr | Phe |
|---|---|---|---|---|---|---|---|---|---|---|---|
| 2 | 0.95(1) | 3.12(3) | 0.88(1) | 5.15(5) | 1.11(1) | | | 1.03(1) | 0.95(1) | 1.00(1) | 0.84(1) | 0.99(1) |
| 3 | | 3.03(3) | | 5.02(5) | 1.03(1) | | 1.01(1) | 0.97(1) | 1.02(1) | 0.93(1) | 0.99(1) |
| 4 | | 1.02(1) | | 5.04(5) | 1.01(1) | | | 0.98(1) | 1.03(1) | 0.89(1) | 1.03(1) |
| 5 | | | | 5.05(5) | 1.04(1) | | | 0.97(1) | 1.01(1) | 0.93(1) | 0.99(1) |
| 6 | | 0.94(1) | | 4.48(4) | 0.94(1) | 0.88(1) | | 0.94(1) | 0.98(1) | 0.89(1) | 0.95(1) |
| 7 | | 0.94(1) | | 4.46(4) | 0.96(1) | 0.89(1) | | 0.92(1) | 0.98(1) | 0.87(1) | 0.98(1) |
| 8 | | 1.03(1) | | 4.00(4) | 1.08(1) | 1.02(1) | | 0.99(1) | 1.01(1) | 0.88(1) | 0.99(1) |
| 9 | | 1.03(1) | | 4.83(5) | 1.08(1) | 1.01(1) | | 0.99(1) | 1.04(1) | | 1.01(1) |
| 10 | | 1.03(1) | | 5.02(5) | 1.00(1) | | | 0.96(1) | 1.01(1) | 0.94(1) | 1.03(1) |
| 11 | | 0.99(1) | | 5.02(5) | 0.98(1) | | 0.98(1) | 0.98(1) | 1.03(1) | 1.02(1) | 1.00(1) |
| 12 | | | | 5.10(5) | 1.01(1) | | | 0.92(1) | 1.03(1) | 0.91(1) | 1.02(1) |
| 13 | | 1.04(1) | | 3.93(4) | 1.11(1) | | | 0.95(1) | 1.03(1) | 0.90(1) | 1.02(1) |
| 14 | | 0.99(1) | | 5.09(5) | 1.00(1) | | 0.99(1) | 1.00(1) | 0.97(1) | 1.89(2) | |
| 15 | | 0.60(1) | | 4.87(5) | 1.14(1) | | 1.04(1) | 0.97(1) | 1.02(1) | 0.94(1) | |
| 16 | | 1.10(1) | | 4.97(5) | 1.07(1) | | | 0.99(1) | 0.94(1) | 1.05(1) | 0.88(1) |
| 17 | | 0.41(1) | | 5.03(5) | 0.99(1) | | | 1.00(1) | 0.96(1) | 1.02(1) | 0.99(1) |
| 18 | | 1.01(1) | | 4.99(5) | | | | 1.00(1) | 1.02(1) | 1.03(1) | 0.90(1) | 1.05(1) |
| 19 | | 1.03(1) | | 4.95(5) | | 0.98(1) | | 1.03(1) | 1.03(1) | 1.02(1) | 0.92(1) | 1.03(1) |
| 20 | | 1.07(1) | | 4.94(5) | | | | 1.02(1) | 1.01(1) | 1.02(1) | 0.93(1) | 1.03(1) |
| 21 | | 1.09(1) | | 4.96(5) | | | | 1.08(1) | 0.96(1) | 0.94(1) | 0.89(1) | 1.09(1) |
| 22 | | 2.42(3) | | 3.07(3) | 2.24(2) | | | 1.05(1) | 1.06(1) | | 1.01(1) | 1.09(1) |

Amino Acids Analysis (6N HCl Hydrolysis; 24 Hrs at 106° C.)

| EXAMPLE NO. | His | Asx | Ser | Glx | Pro | Ala | Gly | Ile | Leu | Tyr | Phe | Lys |
|---|---|---|---|---|---|---|---|---|---|---|---|---|
| 23 | | 3.01(3) | 0.87(1) | 5.10(5) | 1.08(1) | | | 0.96(1) | 1.03(1) | 0.92(1) | 0.99(1) | |
| 24 | | 2.01(2) | | 2.03(2) | 3.02(3) | 1.00(1) | 1.00(1) | 0.95(1) | | 0.99(1) | 0.99(1) | |
| 25 | | 1.07(1) | | 2.03(2) | 3.00(3) | 1.00(1) | | 0.95(1) | | 0.96(1) | 0.99(1) | |
| 26 | | 1.00(1) | | 4.06(4) | 2.01(2) | 0.98(1) | | 0.97(1) | | 1.00(1) | 0.99(1) | |
| 27 | | 1.00(1) | | 5.04(5) | 1.02(1) | 0.97(1) | | 0.98(1) | | 0.99(1) | 1.00(1) | |
| 28 | | 2.01(1) | | 4.03(4) | 1.01(1) | 1.00(1) | | 0.96(1) | | 0.99(1) | 1.01(1) | |
| 29 | | | | 3.08(3) | 3.00(3) | | | 0.96(1) | 1.01(1) | 0.95(1) | | |
| 30 | | 1.03(1) | | 5.03(5) | 0.99(1) | | 1.01(1) | 0.95(1) | 1.03(1) | 0.96(1) | | |
| 31 | | 0.97(1) | | 5.17(5) | 1.00(1) | | 0.95(1) | 0.93(1) | 0.98(1) | * | | |
| 32 | | | | 3.05(3) | 3.00(3) | | | 0.96(1) | 0.99(1) | | | |
| 33 | | 1.02(1) | | 4.03(4) | 1.00(1) | 0.99(1) | | 0.97(1) | 1.02(1) | 0.98(1) | 0.99(1) | |
| 34 | | 1.00(1) | | 5.02(5) | 1.02(1) | 0.99(1) | | 0.97(1) | 1.02(1) | | 0.98(1) | |
| 35 | | 1.01(1) | | 5.00(5) | 1.01(1) | | 1.01(1) | | 2.02(2) | 0.98(1) | 0.98(1) | |
| 36 | | 1.01(1) | | 5.05(5) | 1.00(1) | (Val) 0.97(1) | 1.00(1) | | 1.01(1) | 0.99(1) | 0.99(1) | |
| 37 | | 1.01(1) | | 5.00(5) | 1.02(1) | | 1.00(1) | | 1.01(1) | 0.98(1) | 1.98(2) | |
| 38 | | 1.01(1) | | 4.05(4) | 2.00(2) | | | 0.96(1) | 1.01(1) | 0.97(1) | 0.99(1) | |
| 39 | | | | 4.03(4) | 2.00(2) | | | 0.96(1) | 1.02(1) | 0.99(1) | 0.99(1) | |
| 40 | | 2.10(2) | | 3.00(3) | 1.98(2) | 1.00(1) | 0.97(1) | 0.96(1) | | 0.98(1) | 0.98(1) | |
| 41 | | 3.05(3) | | 4.12(4) | 0.98(1) | 0.99(1) | 0.98(1) | 0.95(1) | | | 1.99(2) | |
| 42 | | 1.00(1) | | 2.04(2) | 1.99(2) | 0.97(1) | | 0.93(1) | | 0.98(1) | 0.98(1) | 1.02(1)** |
| 43 | | 0.98(1) | | 4.08(4) | 1.98(2) | | 0.99(1) | 0.94(1) | | 1.99(2) | 0.99(1) | |
| 44 | | 0.99(1) | | 4.09(4) | 2.02(2) | | | 0.95(1) | | 1.98(2) | 0.98(1) | |
| 45 | | | | 3.08(3) | 2.00(2) | 0.98(1) | | 0.95(1) | | 0.99(1) | 1.00(1) | 1.00(1) |
| 46 | | | | 3.10(3) | 2.00(2) | 0.99(1) | | 0.94(1) | | 0.99(1) | 0.99(1) | 0.99(1) |
| 47 | | | | 3.08(3) | 1.95(2) | 0.98(1) | | 0.97(1) | | 0.99(1) | 0.99(1) | 0.99(1)** |
| 48 | | | | 3.11(3) | 1.98(2) | 0.98(1) | | 0.94(1) | | 1.99(2) | | 0.99(1) |
| 49 | | | | 3.14(3) | 1.97(2) | 0.99(1) | | 0.94(1) | | 0.98(1) | 0.98(1) | 0.99(1) |

-continued

| | | | | | | | | | | | |
|---|---|---|---|---|---|---|---|---|---|---|---|
| 50 | 0.99(1) | | | 3.15(3) | 1.96(2) | 0.99(1) | | 0.96(1) | | 0.99(1) | 0.97(1) |
| 51 | | | | 3.07(3) | 2.01(2) | 0.97(1) | | 0.96(1) | | 1.00(1) | 0.99(1) |
| 52 | | | | 3.11(3) | 1.93(2) | | | 1.00(1) | 1.01(1) | 0.98(1) | 0.98(1) 0.98(1) |
| 53 | | | | 3.14(3) | 1.95(2) | 0.99(1) | | 0.95(1) | | 1.00(1) | 1.00(1) 0.98(1) |
| 54 | | | | 4.08(4) | 1.92(2) | 1.00(1) | | 0.99(1) | | 1.00(1) | 1.00(1) |
| 55 | | | | 4.13(4) | 1.97(2) | 0.96(1) | | 0.96(1) | | 0.98(1) | 0.98(1) |
| 56 | | 0.96(1) | | 3.11(3) | 2.03(2) | 0.98(1) | | 0.94(1) | | 0.98(1) | |
| 57 | | | | 3.00(3) | 2.10(2) | 0.98(1) | 0.97(1) | 0.95(1) | | 0.95(1) | 0.96(1) |
| 58† | 1.01(1) | 2.00(2) | 0.81(1) | 5.93(6) | 3.02(3) | | 1.04(1) | 0.98(1) | 1.05(1) | 0.96(1) | 1.02(1) 1.02(1) |
| 59†† | 1.02(1) | 4.05(4) | 0.92(1) | 6.01(6) | 3.14(3) | | 1.05(1) | 0.98(1) | 1.03(1) | 0.84(1) | 1.02(1) |
| 60 | | 0.98(1) | | 2.06(2) | 2.03(2) | 0.98(1) | | 0.95(1) | | 0.85(1) | |
| 61 | | | | 4.09(4) | 2.00(2) | | | 0.93(1) | | 1.98(2) | |
| 62 | *** | | | 4.06(4) | 2.97(3) | | | 0.96(1) | | 1.00(1) | |
| 63 | *** | | | 4.07(4) | 2.98(3) | | | 0.96(1) | | | |

*(Me)Tyr coelutes but not quantitated.
**(Orn standard used to quantitate)
***Cha present, not calculated
****Tha present, not calculated
†Thr 0.99(1)
††Thr 0.95(1)

Physical Characteristics

| EXAMPLE NO. | HPLC $t_r$ (min) (15–40% gradient) | TLC I (Rf) | TLC II (Rf) | TLC III (Rf) | FAB-MS (M + H) | 280 |
|---|---|---|---|---|---|---|
| 2 | | | | | 1963 | |
| 3 | 14.3 | 0.33 | 0.33 | 0.70 | 1698 | 1203 |
| 4 | 14.2 | 0.44 | 0.39 | 0.74 | 1412 | 1395 |
| 5 | 12.6 | 0.51 | 0.43 | 0.72 | 1296 | 1210 |
| 6 | 14.3 | 0.54 | 0.78 | 0.84 | 1354 | 1235 |
| 7 | 14.2 | 0.51 | 0.72 | 0.83 | 1354 | 1309 |
| 8 | 18.5 | 0.53 | 0.77 | 0.82 | 1355 | 1177 |
| 9 | 12.5 | 0.42 | 0.57 | 0.77 | 1321 | N.D. |
| 10 | 17.1 | | | | 1453 | 1548 |
| 11 | 16.7 | | | | 1511 | 1538 |
| 12 | 18.4 | | | | 1397 | 1438 |
| 13 | 14.0 | | | | 1282 | 1341 |
| 14 | 12.6 | | | | 1485 | 2693 |
| 15 | 15.3 | | | | 1507 | 3691 |
| 16 | 15.7 | | | | 1502 | 2191 |
| 17 | 15.0 | | | | 1514 | 7380 |
| 18 | 12.9 | | | | 1442 | 739 |
| 19 | 15.6 | | | | 1442 | 1285 |
| 20 | 11.8 | | | | 1484 | 1092 |
| 21 | 19.0 | | | | 1518 | 1490 |
| 22 | 10.0 | | | | 1496 | 1135 |
| 23 | 13.7 | | | | 1921 | 1160 |
| 24 | 10.7 | | | | 1347 | 1318 |
| 25 | 13.7 | | | | 1276 | 1187 |
| 26 | 10.0 | | | | 1337 | 1831 |
| 27 | 9.9 | | | | 1370 | 1305 |
| 28 | 8.8 | | | | 1355 | 1265 |
| 29 | 17.8 | | | | 1333 | 1004 |
| 30 | 13.6 | | | | 1474 | 1330 |
| 31 | 14.8 | | | | 1530* | 2373 |
| 32 | 12.6 | | | | 1057 | N.D. |
| 33 | 13.63 | | | | 1353.5 | 1342 |
| 34 | 11.77 | | | | 1319.5 | |
| 35 | 14.00 | | | | 1468.7 | 1320 |
| 36 | 12.18 | | | | 1454.5 | 1399 |
| 37 | 14.73 | | | | 1502.5 | 1405 |
| 38 | 14.72 | | | | 1379.6 | 1363 |
| 39 | 17.43 | | | | 1364.5 | 1191 |
| 40 | 10.02 | | | | 1381.7 | 1157 |
| 41 | 12.83 | | | | 1512.7 | |
| 42 | 11.20 | | | | 1235.6 | 1285 |
| 43 | 11.50 | | | | 1486.7 | 2964 |
| 44 | 12.28 | | | | 1429.9 | 3007 |
| 45 | 12.07 | | | | 1321.7 | 1221 |
| 46 | 12.17 | | | | 1321.7 | 1162 |
| 47 | 11.85 | | | | 1307.6 | 1183 |
| 48 | 8.78 | | | | 1337.7 | 2236 |
| 49 | 12.20 | | | | 1322.9 | 1290 |
| 50 | 5.53 | | | | 1311.6 | 1197 |
| 51 | 15.50 | | | | 1327.6 | 1216 |
| 52 | 17.27 | | | | 1364.1 | 1388 |
| 53 | 10.92 | | | | 1320.9 | 1083 |
| 54 | 13.25 | | | | 1323.7 | 1021 |
| 55 | 12.81 | | | | 1322 | 893 |

-continued

| | | | |
|---|---|---|---|
| 56 | 15.65 | 1315.6 | 1459 |
| 57 | 9.83 | 1367.7 | 1141 |
| 58 | 13.70 | 2513.9 | 1297 |
| 59 | 14.03 | 2501 | |
| 60 | 15.83 | 1185 | |
| 61 | 18.02 | 1420 | |
| 62 | 16.85 | 1345.6 | |
| 63 | 19.08 | 1377* | |

*(M + Na)

The peptides of examples 64–68 have the following properties:

Physical Characteristics

| EXAMPLE NO. | HPLC t$_r$ (min) (15–40% gradient) | FAB-MS (M + H) |
|---|---|---|
| 64 | 21.91 | 1363 |
| 65 | 15.6 | 1329.5 |
| 66 | 16.8 | 1327 |
| 67 | 15.6 | 1343 |
| 68 | 15.9 | 1327 |

| EXAMPLE NO. | Amino Acids Analysis (6N HCl Hydrolysis; 24 Hrs at 106° C.) | | | | |
|---|---|---|---|---|---|
| | Glx | Pro | Ala | Ile | Tyr |
| 64 | 4.03(4) | 1.99(2) | 1.00(1) | 0.96(1) | 0(0) |
| 65 | 4.06(4) | 1.98(2) | 1.02(1) | 0.95(1) | 0.98(1) |
| 66 | 3.99(4) | 2.04(2) | 0.97(1) | 0.94(1) | 1.05(1) |
| 67 | 4.04(4) | 2.04(2) | 0.98(1) | 0.96(1) | 0.98(1) |
| 68 | 4.08(4) | 2.01(2) | 1.01(1) | 0.93(1) | 0.96(1) |

We claim:
1. A peptide derivative of the formula

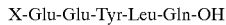

X-Glu-Glu-Tyr-Leu-Gln-OH wherein X is selected from the group consisting of:
H-Gly-Asp-Phe-Glu-Glu-Ile-Pro-;
Ac-Ser-His-Asn-Asp-Gly-Asp-Phe-Glu-Glu-Ile-Pro-;
H-Asn-Asp-Gly-Asp-Phe-Glu-Glu-Ile-Pro-;
H-Asp-Phe-Glu-Glu-Ile-Pro-;
H-Phe-Glu-Glu-Ile-Pro-;
Ac-Asp-Phe-Glu-Glu-Ile-Pro-;
Ac-Gly-Asp-Phe-Glu-Glu-Ile-Pro-;
Suc-Phe-Glu-Glu-Ile-Pro-;
H-Ser-His-Asn-Asp-Gly-Asp-Phe-Glu-Glu-Ile-Pro-;
Ac-Thr-Pro-Asn-Pro-Glu-Ser-His-Asn-Asn-Gly-Asp-Phe-Glu-Glu-Ile-Pro-;
H-Gly-Asp-Phe-Glu-Glu-Ile-Sar-;
H-Gly-Asp-Phe-Glu-Glu-Ile-D-Ala-;
H-Gly-Asp-Phe-Glu-Glu-Ile-Hyp-;
H-Gly-Asp-Phe-Glu-Glu-Ile-NMePgl-;
H-Asp-Phe-Glu-Ala-Ile-Pro-;
H-Gly-Asp-Tyr-Glu-Glu-Ile-Pro-;
H-Gly-Asp-Trp-Glu-Glu-Ile-Pro-;
H-Gly-Asp-pClPhe-Glu-Glu-Ile-Pro-;
H-Gly-Asp-pNO$_2$Phe-Glu-Glu-Ile-Pro-;
H-Gly-Asp-β-(2-thienyl)alanyl-Glu-Glu-Ile-Pro-;
H-Gly-Ala-O-methyltyrosyl-Glu-Glu-Ile-Pro-;
H-Asp-Phe-Glu-Pro-Ile-Pro-; and
Suc-Phe-Glu-Pro-Ile-Pro-.
2. The peptide according to claim 1, wherein X is H-Gly-Asp-Phe-Glu-Glu-Ile-Pro-.
3. The peptide according to claim 1, wherein X is Ac-Ser-His-Asn-Asp-Gly-Asp-Phe-Glu-Glu-Ile-Pro-.
4. The peptide according to claim 1, wherein X is H-Asn-Asp-Gly-Asp-Phe-Glu-Glu-Ile-Pro-.
5. The peptide according to claim 1, wherein X is H-Asp-Phe-Glu-Glu-Ile-Pro-.
6. The peptide according to claim 1, wherein X is H-Phe-Glu-Glu-Ile-Pro-.
7. The peptide according to claim 1, wherein X is Ac-Asp-Phe-Glu-Glu-Ile-Pro-.
8. The peptide according to claim 1, wherein X is Ac-Gly-Asp-Phe-Glu-Glu-Ile-Pro-.
9. The peptide according to claim 1, wherein X is Suc-Phe-Glu-Glu-Ile-Pro-.
10. The peptide according to claim 1, wherein X is H-Ser-His-Asn-Asp-Gly-Asp-Phe-Glu-Glu-Ile-Pro-.
11. The peptide according to claim 1, wherein X is Ac-Thr-Pro-Asn-Pro-Glu-Ser-His-Asn-Asn-Gly-Asp-Phe-Glu-Glu-Ile-Pro-.
12. The peptide according to claim 1, wherein X is H-Gly-Asp-Phe-Glu-Glu-Ile-Sar-.
13. The peptide according to claim 1, wherein X is H-Gly-Asp-Phe-Glu-Glu-Ile-D-Ala-.
14. The peptide according to claim 1, wherein X is H-Gly-Asp-Phe-Glu-Glu-Ile-Hyp-.
15. The peptide according to claim 1, wherein X is H-Gly-Asp-Phe-Glu-Glu-Ile-NMePgl-.
16. The peptide according to claim 1, wherein X is H-Asp-Phe-Glu-Ala-Ile-Pro-.
17. The peptide according to claim 1, wherein X is H-Gly-Asp-Tyr-Glu-Glu-Ile-Pro-.
18. The peptide according to claim 1, wherein X is H-Gly-Asp-Trp-Glu-Glu-Ile-Pro-.
19. The peptide according to claim 1, wherein X is H-Gly-Asp-pClPhe-Glu-Glu-Ile-Pro-.
20. The peptide according to claim 1, wherein X is H-Gly-Asp-pNO$_2$Phe-Glu-Glu-Ile-Pro-.
21. The peptide according to claim 1, wherein X is H-Gly-Asp-β-(2-thienyl)alanyl-Glu-Glu-Ile-Pro-.
22. The peptide according to claim 1, wherein X is H-Gly-Ala-O-methyltyrosyl-Glu-Glu-Ile-Pro-.
23. The peptide according to claim 1, wherein X is H-Asp-Phe-Glu-Pro-Ile-Pro-.
24. The peptide according to claim 1, wherein X is Suc-Phe-Glu-Pro-Ile-Pro-.
25. A peptide derivative of the formula

H-Gly-Asp-Phe-Glu-X wherein X is selected from the group consisting of:
-Pro-Ile-Pro-Glu-Asp-Ala-Tyr-Asp-Glu-OH;
-Pro-Ile-Pro-Glu-Asp-Ala-Tyr-Pro-NH$_2$;
-Glu-Leu-Pro-Glu-Glu-Tyr-Leu-Gln-OH;
-Glu-Val-Pro-Glu-Glu-Tyr-Leu-Gln-OH;
-Glu-Phe-Pro-Glu-Glu-Tyr-Leu-Gln-OH;
-Pro-Ile-Pro-Glu-Asp-Ala-Tyr-Glu-OH;
-Glu-Ile-Pro-Glu-Asp-Ala-Phe-Asp-Glu-OH;
-Pro-Ile-Pro-Glu-Glu-Tyr-Tyr-Glu-OH; and -Pro-Ile-Pro-Glu-Asp-Ala-Tyr-D-Asp-OH.

26. The peptide according to claim 25, wherein X is -Pro-Ile-Pro-Glu-Asp-Ala-Tyr-Asp-Glu-OH.

27. The peptide according to claim 25, wherein X is -Pro-Ile-Pro-Glu-Asp-Ala-Tyr-Pro-NH$_2$.

28. The peptide according to claim 25, wherein X is -Glu-Leu-Pro-Glu-Glu-Tyr-Leu-Gln-OH.

29. The peptide according to claim 25, wherein X is -Glu-Val-Pro-Glu-Glu-Tyr-Leu-Gln-OH.

30. The peptide according to claim 25, wherein X is -Glu-Phe-Pro-Glu-Glu-Tyr-Leu-Gln-OH.

31. The peptide according to claim 25, wherein X is -Pro-Ile-Pro-Glu-Asp-Ala-Tyr-Glu-OH.

32. The peptide according to claim 25, wherein X is -Glu-Ile-Pro-Glu-Asp-Ala-Phe-Asp-Glu-OH.

33. The peptide according to claim 25, wherein X is -Pro-Ile-Pro-Glu-Glu-Tyr-Tyr-Glu-OH.

34. The peptide according to claim 25, wherein X is -Pro-Ile-Pro-Glu-Asp-Ala-Tyr-D-Asp-OH.

* * * * *